United States Patent
Blom et al.

[11] Patent Number: 5,698,773
[45] Date of Patent: Dec. 16, 1997

[54] VISCOMETER

[75] Inventors: Cornelis Blom, Hengelo; Kornelis Oebele Van Der Werf, Rekken, both of Netherlands

[73] Assignee: Vaf Instruments B.V., Dordrecht, Netherlands

[21] Appl. No.: 433,524

[22] Filed: May 2, 1995

[30] Foreign Application Priority Data

May 2, 1994 [NL] Netherlands ............... 9400723

[51] Int. Cl.$^6$ ............................................. G01N 11/00
[52] U.S. Cl. .............................. 73/54.18; 73/32 A
[58] Field of Search ..................... 73/54.24, 54.25, 73/54.26, 54.27, 54.28, 54.31, 54.32, 32 A, 54.18, 54.23, 54.29, 54.34

[56] References Cited

U.S. PATENT DOCUMENTS

| | | | |
|---|---|---|---|
| 3,181,348 | 5/1965 | Lewis | 73/54.25 |
| 3,382,706 | 5/1968 | Fitzgerald et al. | 73/54.25 |
| 3,986,388 | 10/1976 | Stolzy | 73/54.27 |
| 4,005,599 | 2/1977 | Schlatter et al. | 73/54.27 |
| 4,648,262 | 3/1987 | Reis et al. | 73/57 |
| 4,754,640 | 7/1988 | Fitzgerald et al. | 73/54 |
| 4,905,499 | 3/1990 | Miura et al. | 73/32 A |
| 5,212,981 | 5/1993 | Laun et al. | 73/54.01 |
| 5,317,908 | 6/1994 | Fitzgerald et al. | 73/54.26 |

FOREIGN PATENT DOCUMENTS

| | | | |
|---|---|---|---|
| WO91/14168 | 9/1991 | WIPO | G01N 11/14 |
| WO93/02347 | 2/1993 | WIPO | G01N 11/16 |

*Primary Examiner*—Hezron E. Williams
*Assistant Examiner*—Jay L. Poltizer
*Attorney, Agent, or Firm*—Young & Thompson

[57] ABSTRACT

A viscometer provided with a transducer for converting a viscosity parameter of a fluid into an electrical signal. The transducer comprises a container, provided with a cavity for the fluid to be measured, a support element firmly connected thereto and an oscillatory device, which at one end is firmly attached to the support element and at the other end has an oscillatory body. An oscillation drive coil powered by alternating current and a constant magnetic field device for generating a constant magnetic field are provided for bringing and maintaining the oscillatory body in oscillation. The transducer is provided with a detection device for detecting the oscillation of the oscillatory body. The constant magnetic field device is arranged such that it is not able to come into contact with the fluid to be measured and the constant magnetic field lines generated by said device are directed towards the oscillatory body. The oscillation drive coil is accommodated in the oscillatory body with its centre line at a small angle with respect to the constant magnetic field lines.

6 Claims, 4 Drawing Sheets

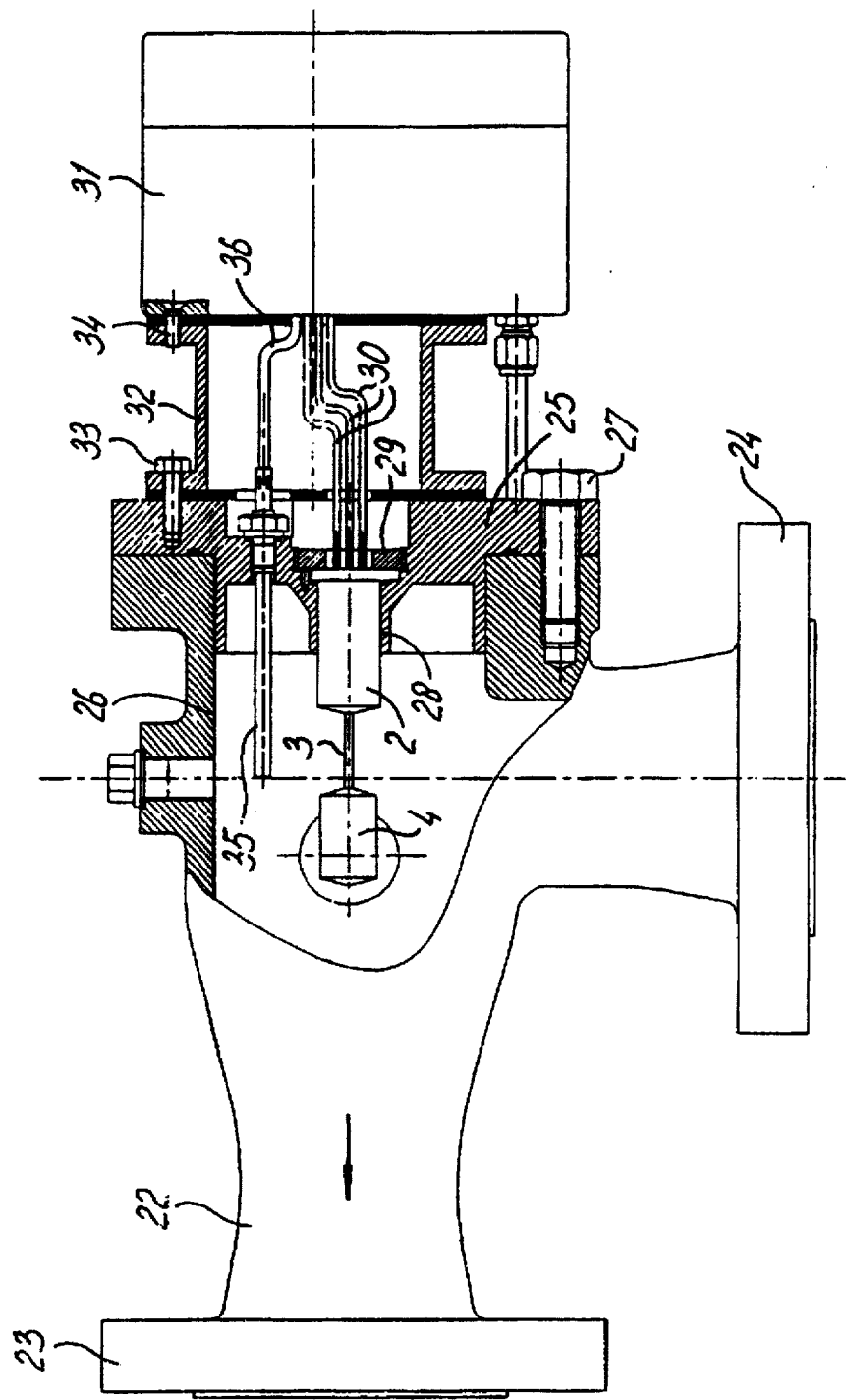

5,698,773

VISCOMETER

BACKGROUND OF THE INVENTION

1. Field of the Invention

The invention relates to a viscometer provided with a transducer for converting a viscosity parameter of a fluid into an electrical signal, comprising a container, provided with a cavity intended for the fluid to be measured, a support element firmly connected to said container, an oscillatory device, which at one end is firmly attached to the support element and at the other end has an oscillatory body, and, in order to bring and maintain the oscillatory body in oscillation, an oscillation drive coil powered by alternating current and a constant magnetic field device for generating a constant magnetic field, and a detection device for detecting the oscillation of the oscillatory body. A viscometer of this type is disclosed in U.S. Pat. No. 4,005,599.

2. Description of the Related Art

The known transducer is of the torsion type and comprises a housing, to which a support element is firmly attached transversely to the side wall thereof. A torsion device is arranged in the housing, which device consists of an oscillatory body and torsion strips, which oscillatory body is connected at one end by means of the torsion strips to the support element. The other end of the oscillatory body is able to move freely. A permanent magnet is arranged in the oscillatory body, the field lines of said magnet running transversely to the side wall of the meter housing. At least at the location of the permanent magnet the housing is made of a non-magnetic material, so that the field lines of the permanent magnet extend outside the housing. An oscillation drive coil is positioned outside the meter housing at the height of the permanent magnet and at a small angle with respect to the North-South direction of the permanent magnet. By connecting an alternating current to the oscillation drive coil, the oscillatory body is brought essentially into torsional vibration by the interaction of the oscillation drive coil and the permanent magnet.

Furthermore, a detection device, which detects the oscillation of the oscillatory body, is present in the known viscometer. The viscosity parameter is determined from, inter alia, the detection result.

It is generally known that many fluids contain iron particles. In this context, the known device has the disadvantage that the iron particles from the fluid to be measured adhere to the oscillatory body and collect there, as a result of which an additional damping is caused. It has been found that only a small amount of adhering iron particles has a substantial effect on the measurement result. The consequence of this is that the viscometer has to be cleaned frequently. Moreover, as a result of the attractive effect of the permanent magnet, cleaning of the oscillatory body is not simple.

OBJECTS AND SUMMARY OF THE INVENTION

The aim of the invention is to provide a viscometer in which the abovementioned problems are avoided and which is particularly easy to maintain.

The aim is achieved according to the invention in that the constant magnetic field device is arranged such that said device remains out of contact with the fluid to be measured and the constant magnetic field lines generated by said device are directed towards the oscillatory body and in that the oscillation drive coil is accommodated in the oscillatory body with its centre line at a small angle with respect to the constant magnetic field lines.

Consequently, the iron particles will no longer collect on the oscillatory body, with the result that the frequency of cleaning can be appreciably reduced.

In one embodiment of the invention, the constant magnetic field device consists of at least one permanent magnet which is positioned adjacent to the oscillatory body outside the cavity intended for the fluid to be measured. By removing the permanent magnet, the viscometer is easier to clean.

In an embodiment of the invention which is preferably to be used, the constant magnetic field device consists of at least one coil powered by a direct current, which coil is positioned adjacent to the oscillatory body outside the cavity intended for the fluid to be measured, with its centre line directed towards the oscillatory body. With this arrangement, for cleaning it is necessary only to switch off the direct current supply, or an alternating current can be connected to said constant field coil.

In another embodiment of the invention, the detection device is an acceleration detector, the viscosity parameter being determined from the amplitude of the signal emitted by said detector and that of the signal applied to the oscillation drive coil.

In the viscometer disclosed in U.S. Pat. No. 4,005,599, a feedback is used to maintain the torsional vibration of the oscillatory body, wherein the detection device, comprising a piezo-electric crystal, for detection of the oscillation of the oscillatory body is arranged at one end and the oscillation drive coil is arranged at the other end of the feedback loop.

In the case of this known meter, two frequencies are measured which are produced by feedback of the in-phase and phase-shifted signal. Consequently, on changeover a new equilibrium situation has to be reached, which lowers the response speed of the measurement; after all, the measurement at one of the frequencies must be for sufficiently long to keep changeover phenomena low. Moreover, the feedback loop is complex and by the known use and position of the permanent magnet it is a disadvantage that ferromagnetic contaminations from the liquid to be measured will adhere to the cylinder of the viscometer and affect directly the measurement.

A further aim of the invention is further to simplify the viscometer. This simplification is achieved in that, in one embodiment of the invention, the acceleration detector is connected via a phase shifter to the oscillation drive coil. By this means the oscillation is automatically maintained with a very much simpler circuit. In the case of the viscometer according to the invention, an amplitude measurement is used instead of a frequency measurement, as a result of which not only is simpler circuitry possible but it is also possible to measure with better resolution.

In an embodiment which is preferably to be used, the acceleration detector consists of two piezo-electric strips, which run parallel to one another and in a pane extending parallel to the oscillation direction of the oscillatory body, and one end of each strip being firmly attached to the oscillatory body, the points of attachment being located dimetrically opposite one another, whilst the other ends thereof are able to move freely in the oscillation direction of the oscillatory body and face in opposing directions, and in that the outputs of the piezo-electric strips are connected to the respective inputs of an instrumentation amplifier, the output of which is connected to the phase shifter. By this means the influence of the translational vibration of the oscillatory body is eliminated.

It is observed that in the viscometers known form EP-A-0 297 032 and U.S. Pat. No. 4,905,499 a piezo-electric detector is used.

In contrast to present invention, in EP-A-0 297 032 it is spoken of a phase difference measurement for determining the damping. The phase shift is used for determining the frequency shift in function of the phase shift. In present invention, however, a phase shift of 9 degrees is used for obtaining a control in the resonance frequency.

Moreover, in the known construction the control and detection are coupled to a rod not damped by the liquid. A tube arranged around the rod is subjected to the damping of the liquid. By the difference in rigidity of the tube and the rod a coupling of two vibration systems occurs, this in contrast to present invention, in which only one vibration system is active. It is practical impossible to make the rigidity of the rod sufficiently higher than the rigidity of the tube.

The viscometer according to U.S. Pat. No. 4,905,499 cannot be used as flow-through sensor, because a separate mass is used for obtaining a vibration system. According to this invention, however, a sensor is achieved, in which the mass, the drive and the detection are located in the measuring head in order to realize a single mass-spring-system.

BRIEF DESCRIPTION OF THE DRAWINGS

The invention will be explained in more detail below with reference to the drawings. In the drawings:

FIG. 7 shows a side view, partly in cross-section, of an embodiment of the viscometer according to the invention accommodated in a pipeline.

DESCRIPTION OF THE PREFERRED EMBODIMENT

Figure 1:
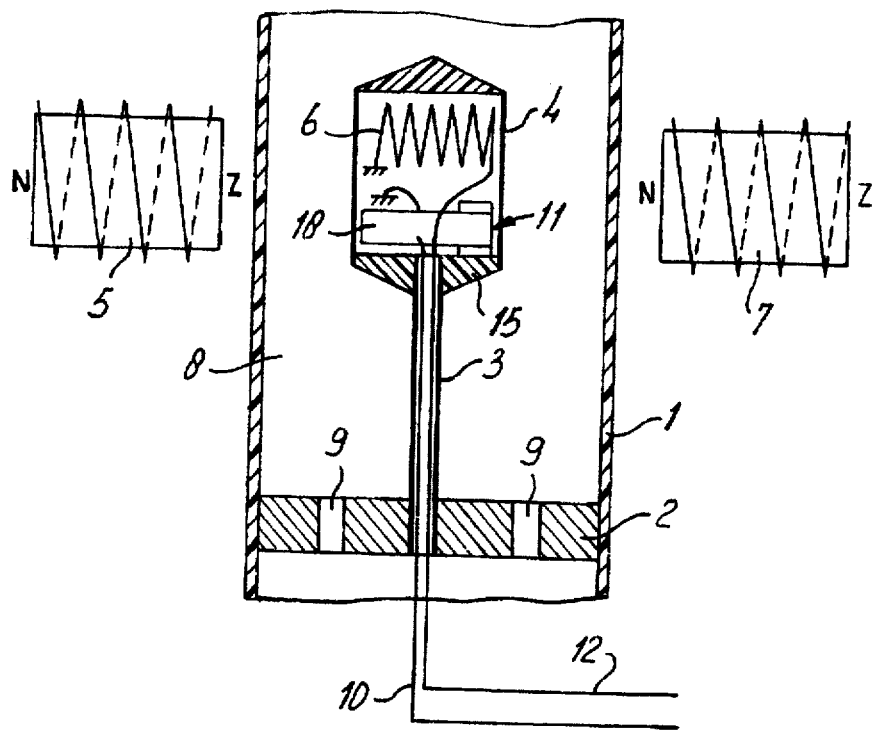
FIG. 1 shows, diagrammatically, an embodiment of the transducer of the viscometer according to the invention.

The invention is based on the insight that a fluid has an effect, in particular a damping effect, on a vibrating oscillatory element which is immersed therein. A feedback system can be used to maintain the oscillatory element in mechanical vibration by supplying energy to the system to compensate for viscous and other inherent mechanical and electrical losses. This is achieved by means of amplifiers in the feedback system. For example, the complex shear viscosity can be determined by measuring the resonance frequency of the oscillatory element and the damping thereof.

Applying the basic concept mentioned above, the viscometer according to the invention is provided by way of an example with a transducer for converting a viscosity parameter of a fluid into an electrical signal. Said transducer comprises a meter housing 1 and a support element or baseplate 2 firmly connected thereto. An oscillatory device is supported by said baseplate 2, which oscillatory device consists of a torsion rod 3, which is rigidly attached to the baseplate 2 and perpendicular thereto, and an oscillatory body 4, which is formed by a cylindrical mass 4, which, in turn, is firmly connected at one end to the free end of the torsion rod 3. The combination of torsion rod 3 and cylindrical mass 4 is brought into the maintained in vibration in a torsion mode. To this end, an excitation system is used which comprises a magnet 5 and a drive coil 6. As can be seen from FIG. 1, the drive coil 6 is accommodated in the cylindrical mass 4, whilst the magnet 5 is positioned outside the housing 1. The mutual orientation of the permanent magnet 5 and the drive coil 6 is such that the centre line of the drive coil is at a small angle with respect to the magnetic field lines of the permanent magnet. Preferably, a second magnet 7 is used.

Figure 6:
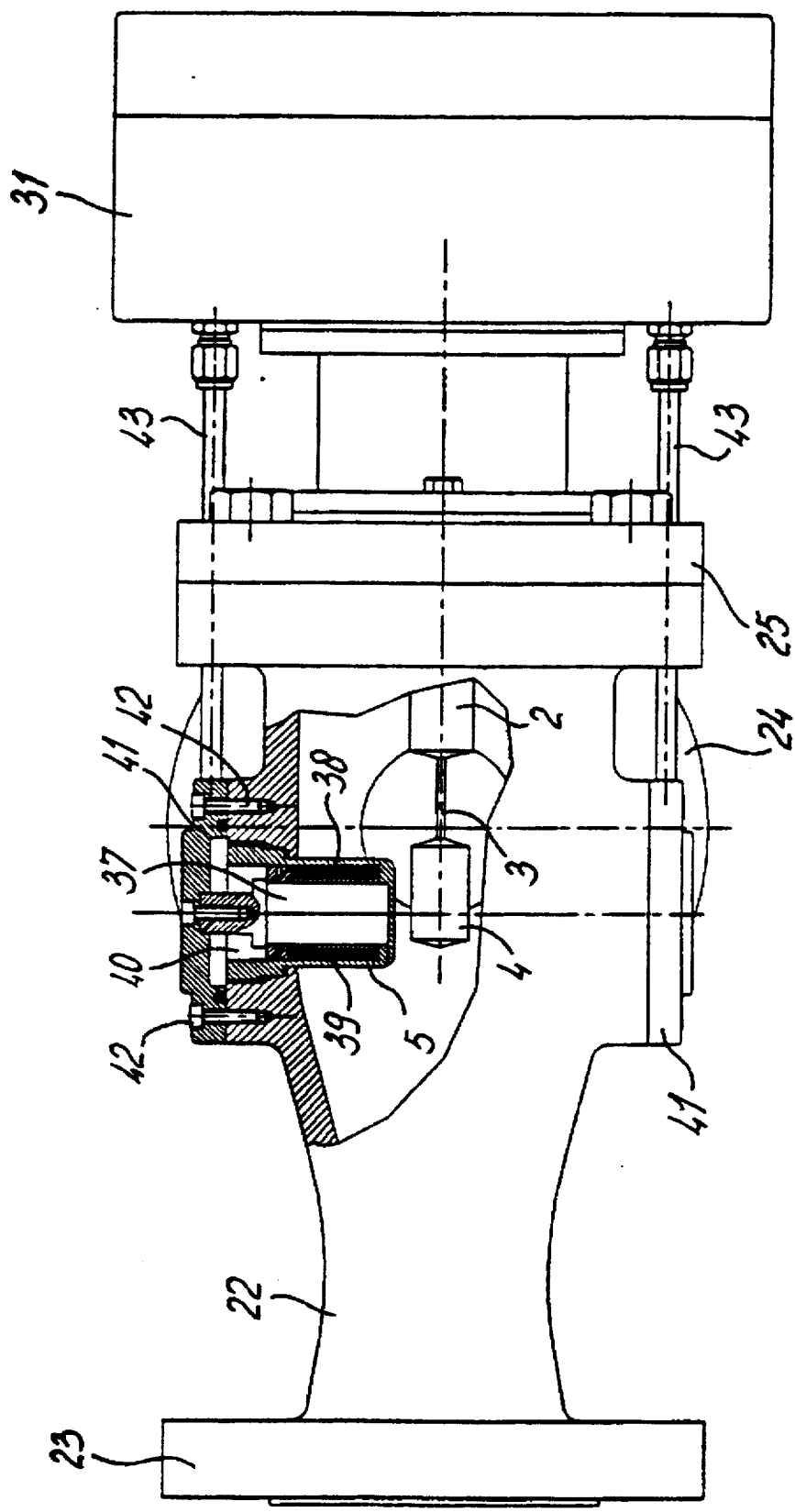
FIG. 6 shows a front view, partially in cross-section, of an embodiment of the viscometer according to the invention accommodated in a pipeline.

In this embodiment the magnet or electromagnet 5 is arranged outside the housing 1, but said magnet can also be accommodated sunken completely or partly into the housing. In this so-called sunken position of the magnet, provision must preferably be made to ensure that the fluid can not come into contact with the magnet, in other words the magnet is located outside the cavity intended for the fluid to be measured and the magnet is thus separated from said cavity. A separated arrangement of the magnet is shown in FIGS. 6 and 7.

At least the cylindrical mass 4 of the oscillatory device is submerged in a fluid or liquid 8, which is present in the cavity which is delimited by the baseplate 2 and a wall, which, for example, is cylindrical, of the housing 1. This viscometer is suitable as a throughflow meter and the liquid to be measured can, for example, be fed in through openings 9 in the baseplate 2, can flow along the torsion rod 3 and the cylindrical mass 4 and can be discharged or reversed by the top opening in the housing 1. The housing 1, with the oscillatory body 4 accommodated therein, can be integrated in a pipe of a pipe system in order to measure a viscosity parameter of the fluid or liquid flowing through the pipe system, continuously or at any desired point in time. For a static measurement, the top opening of the housing can be closed.

Via the supply conductor 12 of the drive coil 6, which is fed through the torsion rod 3, an excitation signal in the form of an alternating current is applied to the drive coil 6. Said excitation signal can, for example, be generated by a frequency generator. The frequency and magnitude of the excitation signal can be controlled by means of a microprocessor. By applying the excitation signal to the drive coil 6, the cylindrical mass 4 is brought into torsional vibration as a result of the interaction of said drive coil 6 with the permanent magnets 5 and 7. In this case, the field lines of the permanent magnets on one side and those of the drive coil 6 on the other side must describe a small angle.

The amplitude of the torsional vibration is measured by means of the detection device 11. The detection output signal from the detection device 11 is ed to the exterior via the output conductor 12 fed through the torsion rod 3. For a fixed excitation signal, the detection signal is a measure of the viscosity of the liquid in which the cylindrical mass is submerged and can be amplified, in a manner which is not shown, filtered by means of a bandpass filter and fed to a voltmeter which is read by the microprocessor.

In the embodiment in FIG. 1, the permanent magnets 5 and 7 are shown as electromagnets, to the coil of which a direct current signal has to be applied.

It is clear that when the permanent magnet is used it is also possible for an effect of collection of iron particles to occur. However, the effect on the measurement is caused only by disturbance of the magnetic field.

The advantage of the viscometer according to FIG. 1 is that this viscometer is particularly easy to maintain becomes the frequency of cleaning is very much lower than in the case of known systems in which the permanent magnet is accommodated in the oscillatory body 4, as a result of which iron particles or other magnetic impurities collect on the oscillatory body. Furthermore, the viscometer can be cleaned easily by removing the permanent magnet 5 or switching off the direct current signal applied to the coil of the permanent electromagnet. The iron particles which have collected can then be removed easily by means of leaning fluid unhindered by magnetic attraction. Consequently, the viscometer is particularly suitable for integration in a pipe system, because the viscometer does not have to be detected from the system in order to remove the oscillatory body 4 therefrom and clean it separately. After all, a cleaning fluid can be fed through the housing 1 of the viscometer without removing the latter from the system. During cleaning both the alternating current signal fed to the supply conductor 10 and the direct current signal applied to the coil of the permanent electromagnet can be switched off. It has been found that cleaning can then take place particularly simply and thoroughly.

The minimum distance between the side surface of the cylindrical mass 4 and the wall of the housing 1 is determined by the requirement that the shear wave must have virtually died away when this reaches the wall 13. For a Newton liquid, the amplitude of the shear wave is attenuated by a factor of 1000 over a distance of 2 mm at a viscosity of 100 mPa and a frequency of 400 Hz.

Figure 2:
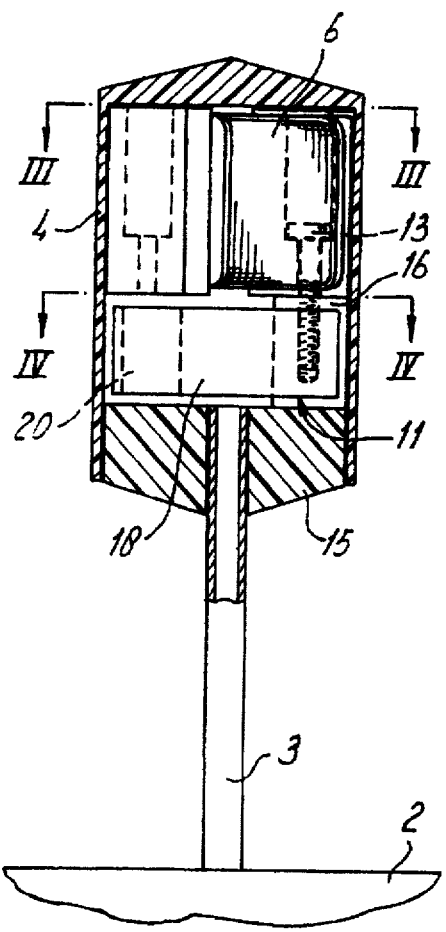
FIG. 2 shows a cross-section through a practical embodiment of the transducer of the viscometer according to the invention.
Figure 3:
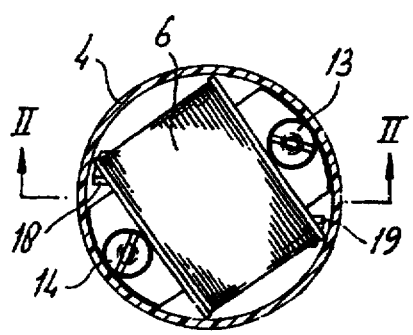
FIG. 3 shows a cross-section along ling III—III in FIG. 2.
Figure 4:
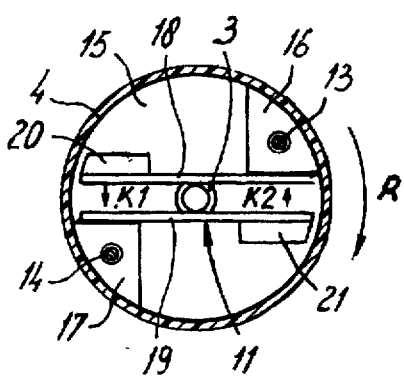
FIG. 4 shows a cross-section along line IV—IV in FIG. 2.

FIGS. 2, 3 and 4 show an oscillatory body according to an embodiment of the invention. In the cross-section in FIG. 2, the supply and return conductors of the coil and the detection device are not shown. The oscillatory body 4 is produced from a non-magnetic or non-magnetisable material. A very suitable material is stainless steel of austenitic structure, such as stainless steel 316. In some applications, a plastic could be adequate. The oscillatory body 4 is closed at the top and bottom. One end of the torsion rod 3 is firmly connected to the bottom closure 15, the other end of said torsion rod being firmly connected to the baseplate 2. In the hosing, the detection device 11 is firmly attached to the housing above the bottom closure 15, as is the drive coil 6 by means of the screws 13 and 14 (FIGS. 2 and 3).

In this embodiment, the detection device 11 is an acceleration detector. An embodiment of the acceleration detector which is preferably to be used can be seen more clearly in FIG. 4. Said acceleration detector comprises two supports 16, 17, which are firmly attached to the oscillatory body. Said supports 16 and 17 support the respective piezo-electric strips 18 and 19 on one side. The other ends of the strips 18 and 19 are able to move freely and are provided with weights 20 and 21 respectively.

When, during the backwards and forwards rotational vibration of the oscillatory body 4 as a consequence of application of an alternating current to the drive coil 6, the oscillatory body 4 rotates, for example in the direction of the arrow R, the forces K1 and, respectively, K2 are exerted on the piezo-electric strips 18 and 19 as a consequence of the inertia of said strips and in particular of the weights 20 and 21 fitted to the free ends thereof. The piezo-electric strips 18 and 19 are bent by the forces K1 and K2, as a result of which a detection output signal is generated by the piezo-electric strips and can be taken off. The viscosity parameter can then be determined from the amplitude of the detection output signal and that of the signal applied to the oscillation drive coil.

However, as an advantageous alternative, an electric feedback circuit can be connected between the drive coil 6 and the detection device consisting of the piezo-electric strips 18 and 19, as a result of which the oscillation in the torison mode of the oscillatory device is automatically maintained, it being possible to determine the viscosity of the fluid or liquid to be measured from the ratio of the amplitude of the detection signal to that of the excitation signal applied to the drive coil 6 by means of, for example, a microprocessor. Said feedback circuit in the measuring circuit of the viscometer according to the invention is shown in FIG. 5.

Figure 5:
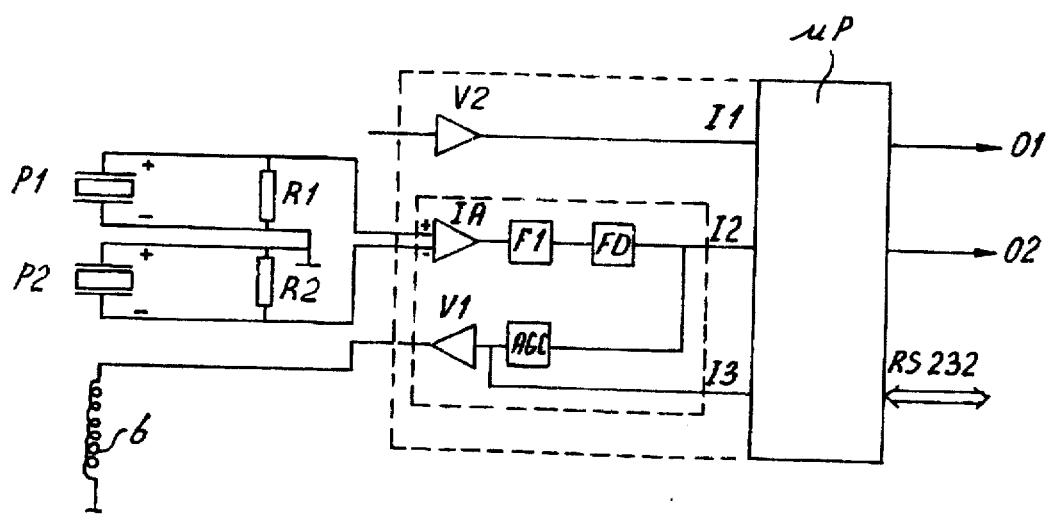
FIG. 5 shows a circuit diagram of the electrical part of the viscometer according to the invention.

In FIG. 5 the piezo-electric strips 18 and 19 are shown diagrammatically as piezo elements and indicated by P1 and P2. The piezo elements P1 and P2 are connected via parallel resistors R1 and R2 to an instrumentation amplifier IA. The polarities are indicated here. In the case of the circuit diagram which is preferably to be used and is shown in FIG. 5, the feedback circuit consists of the said instrumentation amplifier IA, the filter F1, the phase shifter FD, the automatic gain controller AGC and the amplifier V1. The drive coil 6 is connected to the output of the amplifier V1. As a result of the series connection of the piezo elements P1 and P2, the feedback circuit and the drive coil 6, the oscillatory body 4, shown in FIGS. 1, 2, 3 and 4, is brought into and held in vibration in the torsion mode.

The signal which appears at the output of the phase shifter FD and the signal at the junction between the amplifier V1 and the automatic gain controller AGC are fed to the inputs I2 and I3, respectively, of the microprocessor μP, which, on the basis of the ratio of the amplitude of the said signals derives a viscosity output signal which is passed to the output O2. A relationship exists between the viscosity signal at the outut O2 of the microprocessor μP and the signals supplied thereto, which relationship can either be determined experimentally or can be calculated. The signal which originates from a temperature sensor, which is not shown and is arranged in the vicinity of the oscillatory body, is fed to the amplifier V2, the output signal from which is fed to the input I1 of the microprocessor μP. A temperature signal appears at the output O1 of the microprocessor. The signal originating from the temperature sensor can be used by the microprocessor μP to effect a temperature compensation.

In order to keep the mechanical joint between the torsion mass (torsion rod and oscillatory body) and he baseplate 2 as small as possible, the moment of inertia of the baseplate 2 is chosen to be large compared with the moment of inertia of the torsion mass.

All construction materials in the vicinity of the magnets 5 and 7 (see FIG. 1), such as, for example, coil holders, supports, the wall of the housing 1, the wall of the oscillatory body 4 and all supports, are made of non-magnetisable material, such as austenitic stainless steel, for example stainless steel 316, or plastic. Furthermore, preferably materials are chosen which have as low a conductivity as possible, so that the damping of the oscillatory mass as a consequence of eddy current effects is as small as possible.

A significant advantage of the above-described design of the transducer for the viscometer is the very low temperature dependence of the resonance frequency of the oscillatory device, so that, by means of the measured temperature, the microprocessor is easily able to carry out the temperature compensation.

Moreover, the electrical part of the viscometer is very simple and comprises only a small number of components.

The most important advantage of the viscometer according to the invention is that it is very easy to maintain (low cleaning frequency) and that the viscometer does not have to be removed from the integrated system in order to clean the interior of the housing and the oscillatory body.

Furthermore, in particular as a result of the sue of the detection device and the circuit diagram according to FIG. 5, the viscometer according to the invention has the advantage that the translation of the oscillatory body is compensated.

In the case of the translational vibration, which in practice virtually always occurs as a side effect, the piezo-electric strips 18 and 19 will move in opposite directions, so that the voltages which are fed to the instrumentation amplifier IA do not result in a change in output.

In the case of a rotational vibration, which is precisely what is desired in the case of this embodiment, the voltages generated are added and an effect on the output from the amplifier IA is therefore detectable.

FIGS. 6 and 7 show an embodiment of the invention in which the viscometer according to the invention is integrated in a pipe bend or knee 22, which is provided with fixing flanges 23 and 24 for installing the pipe bend 22 in a pipeline system. For illustration, the bend 22 has been cut open at the location of the viscometer. The oscillatory body 4 is connected via the torsion rod 3 to the base 2. The torsion rod 3 and the base 2 are hollow for feeding through the supply and return wires for the drive coil accommodated in the oscillatory body 4 and the piezo-electric strips. The base 2 is firmly connected by means of the blanking element 25 to the bend 22. The blanking element 25 is accommodated in the bore 26 of the band 22 and is screwed firmly to the flange delimiting said opening by means of the screw 27. The base 2 is accommodated in the central bore 28 of the blanking element 25 and is held firmly therein by the retaining nut 29. The supply and return wires issuing from the base 2 run to the electronic circuit of the viscometer incorporated in the housing 31. The housing 31 is screwed by means of a cylindrical connecting piece 32, provided with flanges, by means of the screw 33 and the screw 34 to the blanking element 25. Furthermore, a temperature sensor 35 is also fixed in the blanking element 25 and connected by means of the connecting wire 36 to the associated circuit accommodated in the housing 31 (see FIG. 7). One of the electromagnets 5, 7 arranged adjacent to the oscillatory body 4 on either side can be seen most clearly in FIG. 6. The core 37 of magnetisable material and the associated coil 38 of the electromagnet 5 are accommodated in the housing 39, which components are detachably fixed as a unit in the bore 40 of the housing 39. Fixing is by means of the cap 41 with the associated screws 42. The connecting wires of the direct current coil are fed by means of the protective tube 43 to the associated power supply in the housing 31.

We claim:

1. Viscometer provided with a transducer for converting a viscosity parameter of a fluid into an electrical signal, comprising a container, provided with a cavity intended for the fluid to be measured, a support element firmly connect to said container, an oscillatory device, which at one end is attached to the support element and at another end has an oscillatory body, and in order to bring and maintain the oscillatory body in oscillation, an oscillation drive coil powered by alternating current and a constant magnetic field device for generating a constant magnetic field, and a detection device for detecting the oscillation of the oscillatory body, the constant magnetic field device being disposed such that said device remains out of contact with the fluid to be measured and such that the constant magnetic field lines generated by said device are directed towards the oscillatory body, the oscillation drive coil being accommodated in the oscillatory body with its center line at a small angle with respect to the constant magnetic field lines, the detection device being an acceleration detector consisting of two piezo-electric strips, which run parallel to one another and in a plane extending parallel to the oscillation direction of the oscillatory body, one end of each strip being firmly attached to the oscillatory body, the points of attachment being located diametrically opposite one another, whilst the other end of each strip is able to move freely in the oscillation direction of the oscillatory body and face in opposing directions.

2. Viscometer according to claim 1, wherein the constant magnetic field device comprises at least one permanent magnet positioned adjacent to the oscillatory body outside the cavity intended for the fluid to be measured.

3. Viscometer according to claim 1, wherein the constant magnetic field device comprises at least one coil powered by a direct current which is positioned adjacent to the oscillatory body outside the cavity intended for the fluid to be measured, with its center line directed towards the oscillatory body.

4. Viscometer according to claim 1, wherein the viscosity parameter is determined from the amplitude of the signal emitted by said detector and that of the signal applied to the oscillation drive coil.

5. Viscometer according to claim 4, wherein the acceleration detector is connected via a phase shifter to the oscillation drive coil.

6. Viscometer according to claim 5, wherein the outputs of the piezo-electric strips are connected to the respective inputs of an instrumentation amplifier, the output of which is connected to the phase shifter.

* * * * *